United States Patent
Toyama

[19]
[11] Patent Number: 5,898,182
[45] Date of Patent: Apr. 27, 1999

[54] EXPOSURE MASK CONTAMINATION INSPECT METHOD AND SYSTEM THEREFOR

[75] Inventor: Teruo Toyama, Miyazaki-gun, Japan

[73] Assignee: Oki Electric Industry Co., Ltd., Tokyo, Japan

[21] Appl. No.: 08/923,634

[22] Filed: Sep. 4, 1997

[30] Foreign Application Priority Data

Feb. 4, 1997 [JP] Japan .................................. 9-021670

[51] Int. Cl.⁶ ................................................ G01N 21/86
[52] U.S. Cl. ........................... 250/559.41; 250/548
[58] Field of Search ........................... 250/559.41, 548, 250/222.2; 356/237, 399–401

[56] References Cited

U.S. PATENT DOCUMENTS

5,710,624  1/1998  Utamura ................................ 250/548

*Primary Examiner*—Que T. Le
*Attorney, Agent, or Firm*—Jones, Volentine, Steinberg & Whitt, L.L.P.

[57] ABSTRACT

The present invention provides a method for inspecting only a contamination which there is a possibility to have an actual influence during exposure on a mask. In this method, a mask comprises at least two areas, each of which has a shade pattern, a first inspection light is introduced to the one face of a first area, a second inspection light to another face of a second area. An image transmitting through the first area and an image reflected by the second area are received and composed to obtain a first composite image. Then, an image reflected by the first area and an image transmitting through the second area are received and composed to obtain a second composite image. Thereafter, a contamination on the mask is indicated based on the first composite image and the second composite image.

13 Claims, 4 Drawing Sheets

EXPOSURE MASK CONTAMINATION INSPECT METHOD AND SYSTEM THEREFOR

BACKGROUND OF THE INVENTION

1. Field of the Invention

The present invention relates to a method of inspecting a contamination on an exposure mask used to fabricate an IC (Integrated Circuit), a LSI (Large Scale Integration) and the like and a system therefor, more particularly, relates to a method of inspecting a contamination on a rear face of an exposure mask and a system therefor.

2. Description of the Related Art

Conventionally, there is a technique to inspect a contamination on an exposure mask such as disclosed in Japan Patent Application Laid-Open No. 61-61420 in 1986. In this publication, a laser beam falls on an exposure mask perpendicularly so as to transmit through the exposure mask, and a contamination only on a transmission area is found out by detecting a scattered light which the transmitted light is scattered by a contamination such as dust. A contamination on a rear face is also detected similarly.

In the above-mentioned method, however, since an exposure light is focused on a front face of the exposure mask during exposure, a defocus occurs on the rear face of the mask. Thus, it is impossible to determine whether the size of the contamination detected on the rear face of the exposure mask actually influences on a wafer during transfer (exposure) or not. In this case, there is no choice, but it is determined by experience, or it is determined whether a contamination on the rear face of the exposure mask influences on exposure or not by transferring the mask to a the wafer in practice. Thus, there is a trouble that the detected contamination is judged by the size thereof, and there is a problem that it is impossible to supply good exposure masks efficiently since bad masks are removed after exposing in practice.

Moreover, there is a possibility that a contamination on a rear face of a shade pattern moves into the transmission area by some shock, therefore, it is necessary to detect a contamination not only in the transmission area of the exposure mask but also on the front or rear face of the shade pattern.

Thus, it is desired to detect only a contamination which actually influences on a wafer among contaminations on the rear face of the exposure mask.

SUMMARY OF THE INVENTION

Accordingly, it is an object of the present invention to solve above problems and to provide a system for inspecting a contamination on a mask and a method thereof.

That is, a system of the present invention is used to inspect a contamination on a mask which is formed from one of a transparent member and a shade member and which comprises at least a first area and a second area, each of which includes a common pattern formed from other of a transparent member and a shade member on one surface of the mask. The system comprises a light emission device, a first light receiving element, a second light receiving element, and an indication element (first aspect).

The light emission device (such as a light source) emits a light at least to the first area from the one surface of the mask and to the second area from another surface of the mask.

The first light receiving unit element receives the light transmitting through the first area. The second light receiving element receives the light reflected by the second area.

The indication element (such as an indicator) indicates a contamination on the mask in accordance with the light transmitting through the first area and the light reflected by the second area.

A system may further comprises a first light introduction element and a second light introduction element. The first light introduction element introduces the light to the first area from the one surface of the mask. The second light introduction element introduces the light to the second area from the another surface of the mask (second aspect).

Usually, a large number of same patterns are formed on an exposure mask repeatedly. A light falls on all over this exposure mask so as to expose a resist formed on a wafer, whereby the patterns are transferred on the wafer. Thus, it is possible to fabricate devices of which the number is similar to that of the patterns transferred on the mask at the same time.

For example, an area corresponding to one device is called the first area and an adjacent area corresponding to another device is called the second area in the mask, whereby a contamination on the rear faces of the first area and the second area in the mask is inspected. The inspection light is applied to the front face of the first area, whereby a first transmitting image is obtained from the transmitting light. The inspection light is also applied to the rear face of the second area, whereby a first reflected image is obtained from a first a reflected light. Then, the first transmitting image and the first reflected image are composite. In the first area, a shade pattern and a transmission area are formed similarly to those in the second area. A form and a size in the first area are also similar to those in the second area.

The first transmitting image is data corresponding to a luminous intensity distribution of the transmitting light which is received by applying the inspection light to the first area with the light receiving element arranged at the rear side of the first area. Hereinafter, the data is called a luminous intensity distribution image. The luminous intensity of the transmitting light which passes through the transmission area in the first area is strong, however, that of the inspection light which is blocked off by the shade pattern not to reach the light receiving unit is weak.

When a contamination exists on the rear face of the transmission area in the first area, the inspection light which reaches the contamination is scattered by irregularities of the contamination. Thus, since the inspection light hardly reaches the light receiving unit, the luminous intensity becomes weak. The intensity of the light which passes through the transmission area around the contamination is strong, however, the luminous intensity at the contamination is weak conspicuously in the luminous intensity distribution image. When a contamination exits at the opposite side of the shade pattern in the first area, the inspection light is blocked off by the shade pattern before the inspection light reaches the contamination, therefore, it is impossible to find out the contamination.

The first reflected image is a luminous intensity distribution image of the reflected light received by applying the inspection light to the rear face of the second area with the light receiving element arranged at the rear side of the light receiving element. The inspection light almost passes through the transmission area in the second area and slightly reflects by the mask, therefore, the luminous intensity is weak. On the contrary, the light reflected by the shade pattern reaches the light receiving element, therefore, the luminous intensity is strong.

When a contamination exists on the transmission area in the second area, the inspection light which reaches the contamination is scattered by irregularities of the contamination. Thus, since the inspection light is hardly received by the light receiving element, the luminous intensity is weak. Since the light which is reflected in the transmission area around the contamination is slight, the luminous intensity is weak. Thus, in the luminous intensity distribution image, there is a slight difference between the light densities at the contamination and around it. When a contamination exists at the opposite side of the shade pattern in the second area, the inspection light is scattered by the contamination. Thus, the inspection light is hardly received by the light receiving light, therefore, the luminous intensity is weak.

According to the luminous intensity distribution image, it is possible to find out a position at which a pattern is formed on the front face and the rear face in the inspected area or a position of the contamination. In the second area, the luminous intensity is weak at a position corresponding to the position which the luminous intensity of the transmitting light is strong in the first area. On the contrary, in the second area, the luminous intensity is strong at a position corresponding to the position which the luminous intensity of the transmitting light is weak in the first area. As a result, since the luminous intensity distribution image is a first composite image of the transmitting light and the reflected light, the luminous intensity representing the transmission area and the shade pattern becomes flat and constant. At the position at which a contamination exists, the light densities are weak in both the first transmitting image and the first reflected image, therefore, the luminous intensity is weak though the first transmitting image and the first reflected image are composite. Thus, the first composite image is a luminous intensity distribution image which a variation appears only at the contamination. With the first composite image, it is possible to find out particularly a contamination on the rear face of the transmission area in the first area and a contamination on the opposite side of the shade pattern in the second area. It is impossible to find out a contamination on the opposite side of the shade pattern in the first area, and it is difficult to find out a contamination on the rear face of the transmission area in the second area since the luminous intensity in the transmission area around the contamination is also weak.

Then, a system may further comprises a third light introduction element and a fourth light introduction element. The third light introduction element introduces the light to the first area from the another surface of the mask. The fourth light introduction element introduces the light to the second area from the one surface of the mask. The first light receiving element receives the light reflected by the first area, the second light receiving element receives the light transmitting through the second area, and the indication element indicates a contamination on the mask in accordance with the light transmitting through the second area and the light reflected by the first area (third aspect).

According to the third aspect, it is possible to find out a contamination on the rear faces in the first area and the second area by the transmitting light and the reflected light easily. Thus, it is possible to find out a contamination in the first area and the second area at the same time. That is, the inspection light is applied to the front face of the first area and the rear face of the second area at the same time, and then the inspection light is applied to the rear face of the first area and the front face of the second area at the same time. Thus, it is possible to inspect a mask more rapidly than a case that a front face and a rear face of an area are inspected sequentially, as areas to be inspected increases.

In the system, the first and second light receiving elements may respectively comprise lenses of which magnifications are set so that the indication element indicates only the contamination of a predetermined size and upward (fourth, fifth aspects). The third and fourth light introduction elements may respectively comprise lenses of which magnifications are set so that the indication element indicates only the contamination of a predetermined size and upward (sixth, seventh aspects).

According to the fourth-seventh aspects, the minimum size of a contamination which has an influence when a mask is transferred to a wafer is determined empirically or experimentally, and then the inspection light which passes through an optical lens adjusted at a low magnification is applied to the front face and the rear face of the exposure mask.

A contamination on the rear face of the exposure mask is inspected as above described, whereby it is possible to find out automatically only a contamination which exists on the rear face of the exposure mask and has an actual influence on exposure without finding out a contamination on the front face of the mask and a small contamination which exists on the rear face and has no influence on exposure.

The present invention provides also a method for inspecting a contamination on a mask which is formed from one of a transparent member and a shade member and which comprises at least a first area and a second area, each of which includes a common pattern formed from other of the transparent member and the shade member on one surface of the mask.

In this method, a light is emitted, the light is introduced to a first area from the one face of the mask, and a first image transmitting through the first area is received. A light is introduced to a second area from another surface of the mask, and a second image reflected by the second area is received. The first image and the second image are composed to obtain a first composite image, and the contamination on the mask is indicated based on the first composite image.

This method may be modified as follows.

The light is introduced to the first area from the another face of the mask, and a third image reflected by the first area is received.

A light is introduced to the one surface of the second area, and a fourth image transmitting through the second area is received.

The third image and the fourth image are composed to obtain a second composite image, and the contamination on the mask is indicated based on the second composite image.

This method may be also modified as follows.

The first image is photoelectrically converted to a first electric signal, and the second image is photoelectrically converted to a second electric signal.

The first composite image is photoelectrically converted to a first composite electric signal, and the contamination on the mask is indicated based on the first composite electric signal.

Then, the third image is photoelectrically converted to a third electric signal, the fourth image is photoelectrically converted to a fourth electric signal.

The second composite image is photoelectrically converted to a second composite electric signal, and the contamination on the mask is indicated based on the second composite electric signal.

Then, the contamination is indicated by a variation in the first composite electric signal and/or the second composite electric signal.

Each light received by a light receiving element such as an photoelectric convertor is photoelectrically converted to an electric signal which becomes a higher level as the luminous intensity is strong and a lower level as the luminous intensity is weak. Thus, the electric signal can be obtained as data related to the luminous intensity distribution.

The first inspection light which is applied to the front face of the first area and passes through the transmission area is converted to an electric signal at a high level, and the first inspection light which is reflected by the shade pattern and is not detected is converted to an electric signal at a low level. This electric signal is called a first electric signal.

The second inspection light which is applied to the rear face of the second area and is reflected by the shade pattern is converted to an electric signal at a high level, and the second inspection light which passes through the transmission area is converted to an electric signal at a low level. This electric signal is called a second electric signal.

A third electric signal and a fourth electric signal are also detected in this way.

Then, the value of the first electric signal is added to that of the second electric signal to correspond positions in both areas each other, and the value of the third electric signal is added to that of the fourth electric signal. When the first (third) electric signal is a high level, the second (fourth) electric signal is a low level. On the contrary, when the first (third) electric signal is a low level, the second (fourth) electric signal is a high level. Thus, these signals are added, whereby it is possible to obtain a signal which is constant at a level between the high level and the low level.

At the position which a contamination exists, however, the detected luminous intensity is the lowest level in both the transmitting image and the reflected image as above described. Thus, though the signals are added, the signal level is low. As a result, a variation in the signal appears only by a contamination.

According to the present invention, a contamination is found out by an unique level variation which appears only at the contamination in the first and second composite electric signals which are flat at constant levels.

Thus, when a contamination on a mask with a detailed shade pattern is inspected, there is no variation expect for a contamination. Thus, there is no case that it is difficult to determine whether a signal indicates a contamination or a detailed pattern, therefore, it is possible to detect only a contamination easily.

Additionally, the first, second, third and fourth inspection lights may be obtained from one light source and have one wave length.

BRIEF DESCRIPTION OF THE DRAWINGS

Other objects and advantages of the present invention will become apparent during the following discussion conjunction with the accompanying drawings, in which.

DETAILED DESCRIPTION OF THE PREFERRED EMBODIMENTS

Preferred aspects and embodiments of the present invention will now be described with reference to the accompanying drawings.

Incidentally, all drawings merely illustrate rough forms, sizes and positional relations of elements and members to understand the present invention.

<First Embodiment>

Figure 1A:
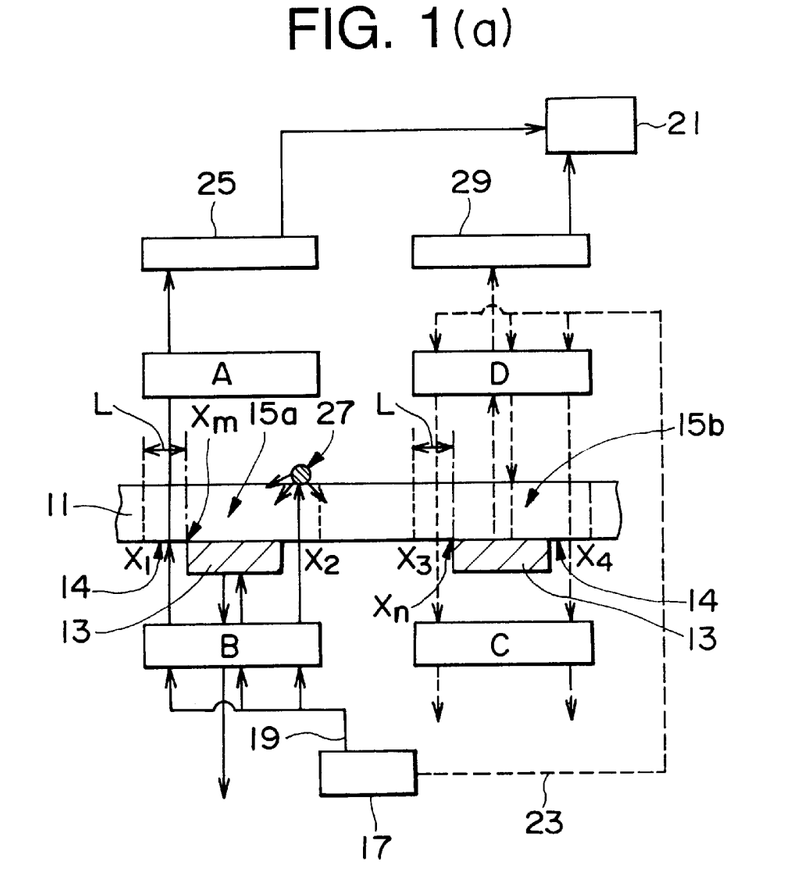
FIG. 1(a) is a sectional view illustrating a mask contamination inspection system of the first embodiment.

An explanation will be given of a case that there is a contamination on transmission area in a rear face of an exposure mask in the first embodiment. FIGS. 1(a) though 2(b) are used to explain the first embodiment. FIG. 3 is a plan view illustrating roughly a part of an exposure mask.

In an exposure mask 11, at least two areas 15, each of which has a specific shade pattern 13 are arranged (see FIG. 3). One area is called a first area 15a, and another area is selected among areas expect for the first area 15a and called a second area 15b. Both the first area 15a and the second area 15b are respectively provided with similar shade patterns 13 and similar transmission areas 14, and a size and a form of the first area 15a are similar to those of the second area 15b.

Now, the contamination inspection is carried out on the rear face of the mask 11 as to the first area 15a and the second area 15b at the same time. The inspection is carried out by moving the exposure mask 11 along a line X—X. The inspection light falls from an irradiation start point $X_1$ to an irradiation end point $X_2$ in the first area 15a and from an irradiation start point $X_3$ to an irradiation end point $X_4$ in the second area 15b on the line X—X, and the exposure mask 11 is sequentially moved along a direction of Y—Y so as to inspect all inspection areas. Here, inspection data obtained by once applying the inspection light to a portion on which there is a contamination are extracted.

FIG. 1(a) is a sectional view illustrating the exposure mask 11 along the line X—X in FIG. 3. First, a first inspection light 19 is applied from a light source 17 through a lens B to the front face of the first area 15a. At the same time, a second inspection light 23 is applied through a lens D to the rear face of the second area 15b (see FIG. 1(a)). The lenses A–D are optical lenses which magnifications are lowered suitably not so as to detect a small contamination which has no actual influence on exposure to the front face of the mask 11 and to the rear face of the mask 11 (100 optical magnification in this embodiment). The lenses A–D are set at the same magnification. A lens which is usually used to inspect whether there is a contamination or not is set at 1000–2000 magnification, however, in this embodiment, since the object is to detect only a contamination which has an actual influence on exposure to the rear face of the mask 11, the magnification of the lens is lowered.

Figure 1B:
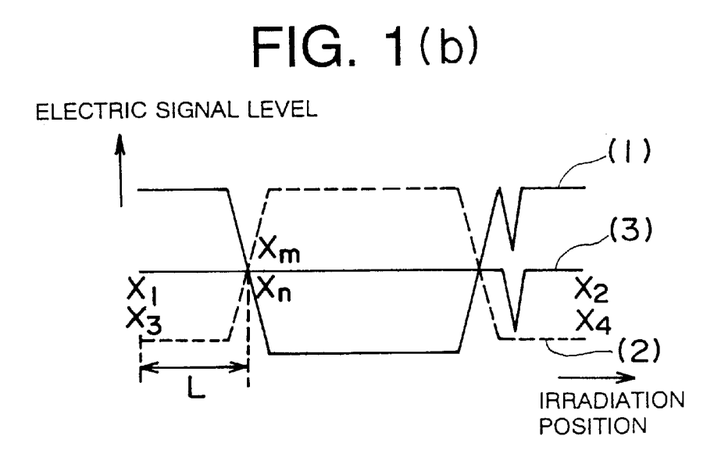
FIG. 1(b) is a characteristic view illustrating electric signals.

FIG. 1(b) is a characteristic view illustrating electric signals obtained by light receiving parts 25, 29 and monitored by an indicator 21 in the inspection system. A horizontal direction indicates a irradiation position, and a longitudinal direction indicates electric signal levels corresponding to the luminous intensity of the detected light. The electric signal level becomes higher, as the luminous intensity becomes stronger. In FIG. 1(b), the detected result in the first area 15a and that in the second area 15b are overlapped. A irradiation distance between the irradiation start point $X_1$ and an irradiation end point $X_2$ in the first area 15a is similar to that between an irradiation start point $X_3$ and an irradiation end point $X_4$ in the second area 15b.

A point at a distance L away from the irradiation start point $X_1$ to the irradiation end point $X_2$ in the first area 15a and a point at a distance L away from the irradiation start point $X_3$ to the irradiation end point $X_4$ in the second area 15b are respectively set as $X_m$ and $X_n$. In FIG. 1(b), the $X_m$ is just over $X_n$. A first electric signal (1) indicates an electric signal to be a detected result in the first area 15a, and a second electric signal (2) indicates an electric signal to be a detected result in the second area 15b. Then, a third electric signal (3) indicates an electric signal composed of the detected result in the first area 15a and that in the second area 15b.

When the first inspection light 19 falls on the front face of the first area 15a from the irradiation start point $X_1$ to the irradiation end point $X_2$, the light 19 passes through the transmission area 14 and reaches a first light receiving part 25 provided at the rear side of the mask 11, whereby an electric signal corresponding to the luminous intensity is detected. This electric signal is the first electric signal (1). As to the first electric signal (1), the light reflected by the shade pattern 13 does not reach the first light receiving part 25, therefore, the electric signal level becomes low. Moreover, the light which reaches a contamination 27 on the rear face of the transmission area 14 in the first area 15a is scattered by irregularities of the contamination 27, therefore, little light reaches the first light receiving part 25. Thus, the electric signal level drops rapidly at the portion of the contamination 27 (see FIG. 1(b)).

The second inspection light 23 falls on the rear face in the second area 15b from the irradiation start point $X_3$ to the irradiation end point $X_4$, whereby the second electric signal (2) is obtained. As to the second electric signal (2), the light 23 passes through the transmission area 14 to the front face, and no light 23 reaches a second light receiving part 29 provided at the rear side of the mask 11, therefore, the electric signal becomes a low level. The light reflected by the shade pattern 13 reaches the second light receiving part 29, therefore, the electric signal of a high level is detected (see FIG. 1(b)).

The first electric signal (1) and the second electric signal (2) are composed, whereby a first composite electric signal (3) is obtained.

The first electric signal (1) is a signal of a transmitting light detected by applying the first inspection light to the front face of the first area 15a. The second electric signal (2) is a signal of a reflected light detected by applying the second inspection light to the rear face of the second area 15b.

The first composite electric signal (3) is a flat signal which there is no difference between the transmission area 14 and the shade pattern 13, since a high level portion of the electric signal in the first area 15a corresponds to a high level portion of the electric signal in the second area 15b and both portions negate each other (see FIG. 1(b)). Then, there is very few cases that contaminations of the same forms and the same sizes exist at the same positions in both the first area 15a and the second area 15b, therefore, there is a variation in the signal at the position which the contamination 27 exists when both signals are composite. Thus, the first electric signal (1) and the second electric signal (2) are composite, whereby it is possible to obtain the first composite electric signal (3) indicating only the contamination 27.

Next, a third electric signal (4) and the fourth electric signal (5) are obtained. The third electric signal (4) is a signal of the reflected light detected by applying a third inspection light 31 to the rear face of the first area 15a. The fourth electric signal (5) is a signal of the transmitting light detected by applying a fourth inspection light 33 to the front face of the second area 15b. The inspection is carried out by the same procedure to obtain signals of the transmitting light in the first area 15a and the reflected light in the second area 15b (see FIG. 2(a)). The inspection lights can be selectively applied to the front face of the mask 11 and to the rear face by mirrors or the like (the reverse is also possible) simply.

As to the third electric signal (4), since the contamination 27 exists at the transmission area 14 in the first area 15a and the electric signal becomes a low level around the contamination 27 in the first area 15a, the contamination 27 stands out not much. Thus, the variation indicating the contamination 27 in the second composite electric signal (6) becomes weak (see FIG. 2(b)).

Figure 2A:
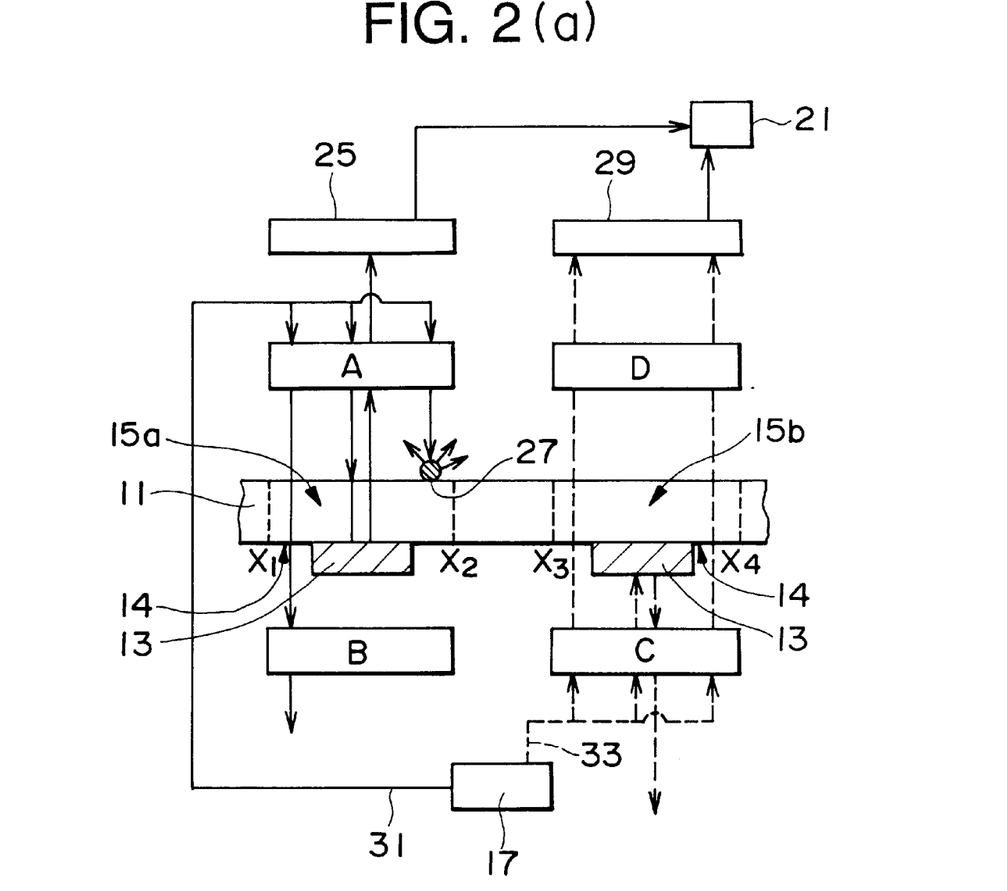
FIG. 2(a) is a sectional view illustrating a mask contamination inspection system of the first embodiment.
Figure 2B:
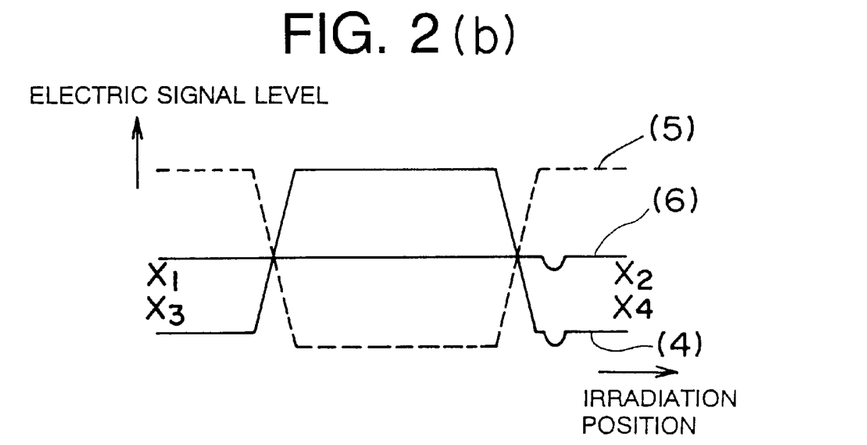
FIG. 2(b) is a characteristic view illustrating electric signals.
Figure 3:
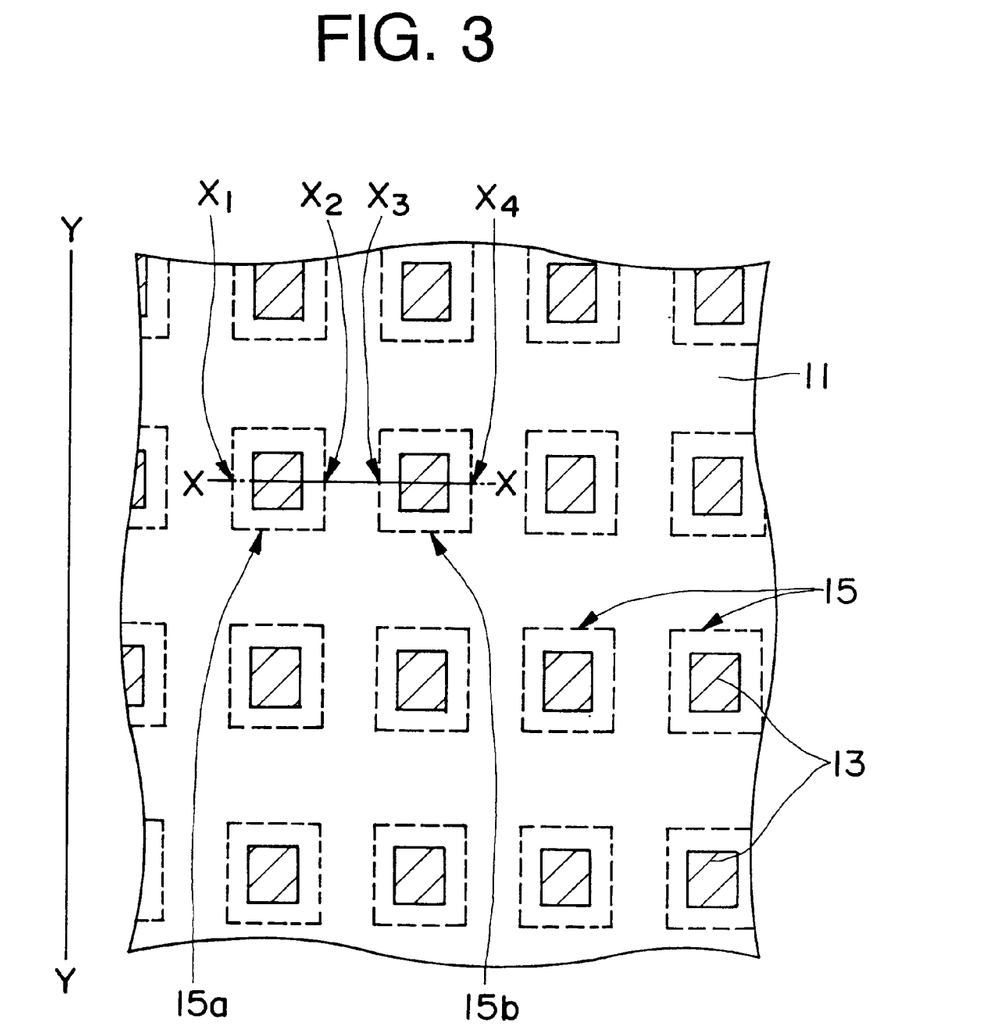
FIG. 3 is a plan view illustrating a part of a surface of an exposure mask.

Thus, it is desired to detect the contamination 27 by comparing and examining the first composite electric signal (3) which is the detected result obtained from the transmitting light in the first area 15a and the reflected light in the second area 15b (see FIG. 1(b)) and the second composite electric signal (6) which is the detected result obtained from the reflected light in the first area 15a and the transmitting light in the second area 15b (see FIG. 2(b)).

As a result, inspection lights are passed through the lenses A–D set at low magnification (about 100 optical magnification in this embodiment), whereby it is possible to automatically detect only a contamination which has an actual influence on exposure, and it is possible to detect only a contamination easily though the shade pattern 13 is detailed and complex.

Further, a light obtained from the same light source such as a mercury lamp of the same wave length (such as 600 nm) is used for the first, second, third and fourth inspection lights.

<Second Embodiment>

Figure 4A:
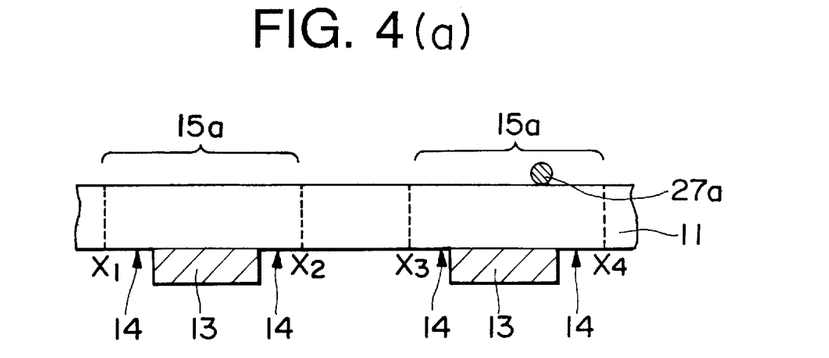
FIG. 4(a) is a sectional view illustrating a mask contamination inspection system of the second embodiment.

An explanation will be given of a contamination inspection method according to the second embodiment in a case that a contamination exists at the opposite side of the shade pattern 13 not at the transmission area 14 with reference to FIGS. 4(a) through 4(c). Forms and sizes of the shade pattern 13 and areas are similar to those in the first embodiment.

Figure 4B:
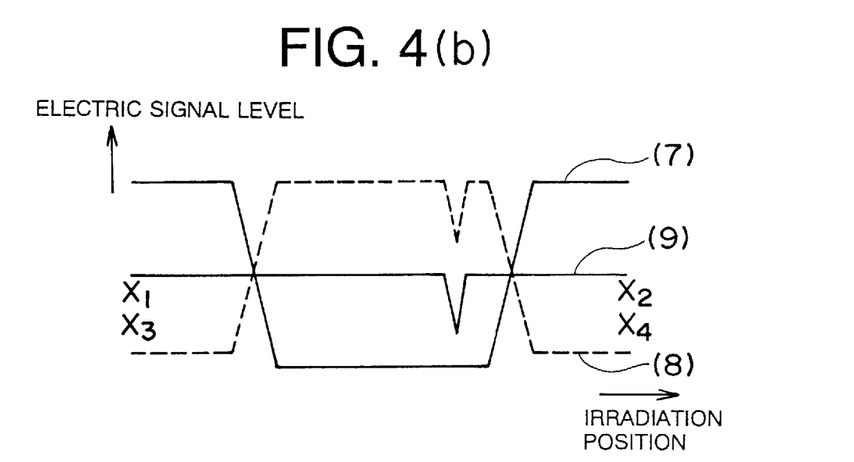
FIGS. 4(b) and 4(c) are characteristic views illustrating electric signals.
Figure 4C:
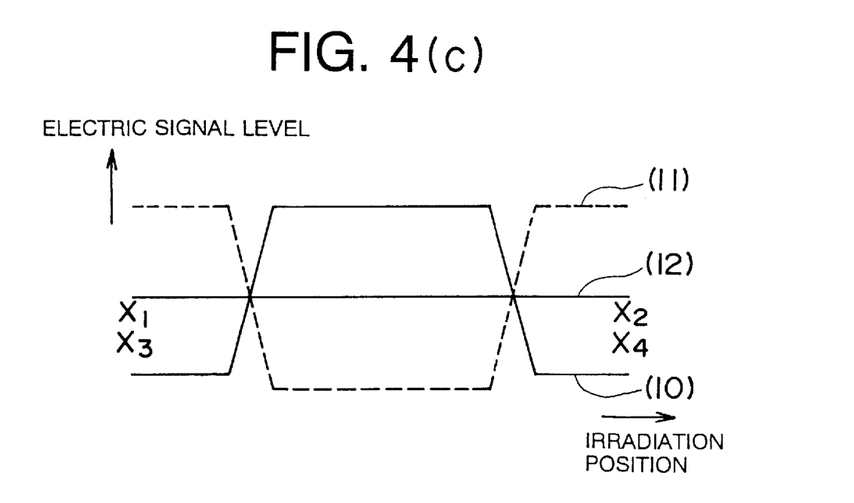

Similarly to the first embodiment, a first electric signal (7) and a second electric signal (8) are composite to obtain a first composite electric signal (9) (see FIG. 4(b)), and then a third electric signal (10) and a fourth electric signal (11) are composite to obtain a second composite electric signal (12) (see FIG. 4(c)).

The first composite electric signal (8) is a detected result obtained from the transmitting light in the first area 15a and the reflected light in the second area 15b. The second composite electric signal (12) is a detected result obtained from the reflected light in the first area 15a and the transmitting light in the second area 15b.

Compared the first composite electric signal (9) and the second composite electric signal (12), the first composite electric signal (9) shows apparently that a contamination 27a exists at the opposite side of the shade pattern, on the contrary, the second composite electric signal (12) does not show the contamination 27a since the fourth inspection light 33 is blocked by the shade pattern 13 in the second area 15b.

There is no case that the contamination 27a directly influences on exposure when the contamination 27a is fixed to the opposite side of the shade pattern 13. It, however, is necessary to detect the contamination 27a since there is a case that the contamination 27a moves to the transmission area 14 with shocks by conveying the mask 11 and so on.

Thus, in this case, the inspection requires to compare the first composite electric signal (9) (see FIG. 4(b)) with the second composite electric signal (12) (see FIG. 4(c)). The first composite electric signal (9) is the detected result obtained from the transmitting light in the first area 15a and the reflected light in the second area 15b. The second composite electric signal (12) is the detected result obtained from the reflected light in the first area 15a and the transmitting light in the second area 15b.

Thus, it is possible to automatically detect only the contamination 27a which there is a possibility of influence on actual exposure among contaminations on the rear face of the exposure mask 11.

As above described, according to the present invention, for the contamination inspection on an exposure mask with at least two areas, each of which has a specific shade pattern, a composite electric signal is obtained by composing the electric signal of the transmitting light detected by applying the inspection light to the front face in one area of the exposure mask and the electric signal of the reflected light detected by applying the inspection light to the rear face in another area of the exposure mask. Then, another composite electric signal is obtained by composing the electric signal of the reflected light detected by applying the inspection light to the rear face in one area of the exposure mask and the electric signal of the transmitting light detected by irradiating the inspection light to the front face in another area of the exposure mask.

Then, since variations in these two composite electric signals represent contaminations on the whole rear face of the mask, it is possible to detect contaminations on the rear face of the mask with detailed and complex shade patterns easily. Moreover, two areas can be inspected at the same time, therefore, it is possible to further shorten the inspection time as the number of areas to be inspected becomes larger.

Further, the inspection lights are passed through optical lenses which magnifications are lowered suitably to detect only a contamination which there is a possibility of an actual influence on exposure, and the inspection lights are applied to the mask, therefore, there is no case to detect a contamination which is unnecessary to be inspected.

Thus, it is possible to shorten a time to determine whether a contamination influences on exposure or not, and it is possible to supply an exposure mask of a high quality.

There is a possibility that a contamination on the opposite side of the shade pattern of the mask moves into the transmission area and influences on exposure with shocks by conveying the mask and so on, however, according to the contamination inspection method of the present invention, it is possible to detect all contaminations at the opposite side of the shade pattern, therefore, there is no possibility that a contamination influences on exposure.

Thus, it is possible to shorten a time to detect a contamination and to determine whether a contamination influences on exposure or not, and it is possible to supply an exposure mask of a high quality.

Additionally, the explanation is given of the case that there is a contamination on a mask in these embodiment, however, it is also possible to detect a flaw, a defect and the like of the mask.

Further, the explanation is given of a positive photo mask in these embodiment, however, it is also possible to apply the present invention to a negative photo mask.

This invention being thus described, it will be obvious that same may be varied in various ways. Saturations are not to be regarded as departure from the spirit and scope of the invention, and all such modifications would be obvious for one skilled in the art intended to be included within the scope of the following claims.

What is claimed is:

1. A system for inspecting a contamination on a mask which is formed from one of a transparent member and a shade member and which comprises at least a first area and a second area, each of which includes a common pattern formed from other of the transparent member and the shade member on one surface of the mask, said system comprising:
   a light emission device emitting a light at least to the first area from the one surface of the mask and to the second area from another surface of the mask;
   a first light receiving element receiving the light transmitting through the first area;
   a second light receiving element receiving the light reflected by the second area; and
   an indication element indicating a contamination on the mask in accordance with the light transmitting through the first area and the light reflected by the second area.

2. A system according to the claim 1, further comprising:
   a first light introduction element introducing the light to the first area from the one surface of the mask; and
   a second light introduction element introducing the light to the second area from the another surface of the mask.

3. A system according to the claim 2, further comprising:
   a third light introduction element introducing the light to the first area from the another surface of the mask;
   a fourth light introduction element introducing the light to the second area from the one surface of the mask;
   wherein said first light receiving element receives the light reflected by the first area, said second light receiving element receives the light transmitting through the second area, and said indication element indicates a contamination on the mask in accordance with the light transmitting through the second area and the light reflected by the first area.

4. A system according to the claim 1; wherein said first light receiving element comprises a lens of which a magnification is set so that said indication element indicates only the contamination of a predetermined size and upward.

5. A system according to the claim 1; wherein said second light receiving element comprises a lens of which a magnification is set so that said indication element indicates only the contamination of a predetermined size and upward.

6. A system according to the claim 3; wherein said first light introduction element comprises a lens of which a magnification is set so that said indication element indicates only the contamination of a predetermined size and upward.

7. A system according to the claim 3; wherein said fourth light introduction element comprises a lens of which a magnification is set so that said indication element indicates only the contamination of a predetermined size and upward.

8. A method for inspecting a contamination on a mask which is formed from one of a transparent member and a shade member and which comprises at least a first area and a second area, each of which includes a common pattern formed from other of the transparent member and the shade member on one surface of the mask, said method comprising:

a step of emitting a light;

a step of introducing the light to the first area from the one surface of the mask;

a step of receiving a first image transmitting through the first area;

a step of introducing the light to the second area from another surface of the mask;

a step of receiving a second image reflected by the second area;

a step of composing the first image and the second image to obtain a first composite image; and a step of indicating the contamination on the mask based on the first composite image.

9. A method according to the claim 8, further comprising:

a step of introducing the light to the first area from the another surface of the mask;

a step of receiving a third image from the first area;

a step of introducing the light to the second area from the one surface of the mask;

a step of receiving a fourth image from the second area;

a step of composing the third image and the fourth image to obtain a second composite image; and a step of indicating the contamination on the mask based on the second composite image.

10. A method according to the claim 8, further comprising:

a step of photoelectrically converting the first image to a first electric signal;

a step of photoelectrically converting the second image to a second electric signal;

a step of photoelectrically converting the first composite image to a first composite electric signal; and a step of indicating the contamination on the mask based on the first composite electric signal.

11. A method according to the claim 9, further comprising:

a step of photoelectrically converting the third image to a third electric signal;

a step of photoelectrically converting the fourth image to a fourth electric signal;

a step of photoelectrically converting the second composite image to a second composite electric signal; and a step of indicating the contamination on the mask based on the second composite electric signal.

12. A method according to the claim 8, wherein the contamination is indicated by a variation in the first composite electric signal.

13. A method according to the claim 9, wherein the contamination is indicated by a variation in the second composite electric signal.

* * * * *